(12) United States Patent
Phillips et al.

(10) Patent No.: US 12,005,197 B1
(45) Date of Patent: Jun. 11, 2024

(54) UROLOGICAL DEVICE THAT PROVIDES GUIDED PLACEMENT FOR AN INDWELLING CATHETER

(71) Applicants: Delmarva Sharpening Service, Inc., Salisbury, MD (US); Ouron Medical Inc., Salisbury, MD (US)

(72) Inventors: Jeffrey Phillips, Salisbury, MD (US); Joy Maulik, Salisbury, MD (US)

(73) Assignees: Ouron Medical Inc., Salisbury, MD (US); Delmarva Sharpening Service, Inc., Salisbury, MD (US)

( * ) Notice: Subject to any disclaimer, the term of this patent is extended or adjusted under 35 U.S.C. 154(b) by 0 days.

(21) Appl. No.: 18/586,994

(22) Filed: Feb. 26, 2024

(51) Int. Cl.
*A61M 25/01* (2006.01)
*A61M 25/00* (2006.01)
*A61M 25/09* (2006.01)
*A61M 39/10* (2006.01)

(52) U.S. Cl.
CPC ........ *A61M 25/0017* (2013.01); *A61M 25/01* (2013.01); *A61M 25/09* (2013.01); *A61M 39/10* (2013.01)

(58) Field of Classification Search
CPC .......... A61M 25/0017; A61M 25/0023; A61M 25/01; A61M 25/0169; A61M 25/09; A61M 39/10
See application file for complete search history.

(56) References Cited

U.S. PATENT DOCUMENTS

| 6,682,536 B2 * | 1/2004 | Vardi | ...................... A61F 2/954 606/108 |
| 9,925,357 B2 * | 3/2018 | Lafitte | ............... A61M 25/0169 |

* cited by examiner

*Primary Examiner* — Catharine L Anderson
(74) *Attorney, Agent, or Firm* — Larry J. Guffey, Esq.; Oliver & Grimsley, LLC

(57) ABSTRACT

A urological device, that provides for the guided placement of the distal end of an indwelling catheter into a patient's bladder, includes: (a) a cylinder whose proximal end has a larger diameter than its distal end, (b) a confirmation lumen in the cylinder that is configured to allow for drainage of urine from a patient's bladder to confirm the necessary placement of the device's distal end in a patient's bladder, (c) a guide wire lumen in the cylinder that extends between its ends, (d) a guide wire, and (e) wherein the guide wire lumen is configured to first allow for the passage of the guide wire's distal end through the guide wire lumen and into the patient's bladder and then the withdrawal of the cylinder from the patient's urethra while leaving behind the guide wire's distal end in the patient's urethra for use in the insertion of an indwelling catheter.

20 Claims, 2 Drawing Sheets

UROLOGICAL DEVICE THAT PROVIDES GUIDED PLACEMENT FOR AN INDWELLING CATHETER

BACKGROUND OF THE INVENTION

1. Field of the Invention

The present invention generally relates to devices for introducing media into the body. More particularly, this invention relates to an improved urological device that provides guided placement for an indwelling catheter.

2. Description of the Related Art

A urethral catheterization that involves passing the distal end of an indwelling catheter (e.g., a Foley catheter) through a patient's urethra and into one's bladder can be difficult for various reasons, including encountering a false passage created during a past catheter placement attempt, prior urethral trauma resulting in a urethral stricture, enlargement of the prostate gland (e.g., benign prostatic hyperplasia), or prior surgery or treatment on the urinary tract. In these scenarios, urologists are often called to the operating room or bedside to assist with the placement of such catheters.

These difficult urethral catheterizations often require additional equipment such as smaller, specialty guide wires that, because of their size, can more easily find a passage through a patient's urethra and into one's bladder. These are then used with followers/dilators to expand the found passageway before the insertion of an indwelling catheter is again attempted.

The guide wires themselves are typically long, thin, flexible wires that are made from a biocompatible material (e.g., polytetrafluoroethylene, PTFE). They are often referred by the size of the wire's diameter which is often denoted in terms of a French scale or gauge, Fr. For example, a wire having a diameter of 0.039 inches is denoted as a 3 Fr size (where a Fr equals 0.013 inches or 0.33 mm). Such guide wires often have sizes in the range of 2-6 Fr.

Such guide wire's proximal end typically has a connector that allows the guide wire to be attached to the distal end of a dilator or follower which is of a larger, varying diameter (e.g., 10-24 Fr, with the proximal end diameter being larger than that of the distal end) and therefor capable, with its passage through a patient's urethra, of expanding the diameter of the hole made by the guide wire's passage. Such dilators will also usually have a drain lumen that extends between their ends and with an opening at their distal end that allows urine to enter the drain lumen, pass through it, and exit at a port that is proximate the dilator's proximal end.

Meanwhile, these guide wires often have a filiform tip which has an even smaller diameter (e.g., 1-3 Fr) and a tapered free end that allows it to better navigate through narrow or tortuous pathways with greater ease. The filiform tip is typically made of a softer, more flexible, biocompatible material than the rest of the guide wire, allowing it to better bend and conform to the contours of the urethra's internal structures.

However, despite this prior art, and after the above-described equipment has been used to dilate a possible passage through the urethra which may then be used to insert an indwelling catheter into a patient's bladder, this final step does not always go smoothly as insertion problem are still often encountered. When this situation occurs, an operative (with the patient under a general anesthesia) procedure using a flexible cystoscope is often used to try to insert the indwelling catheter. Thus, the need exists for an improved, urological device that can provide better guidance for such an insertion of an indwelling catheter.

DESCRIPTION OF THE PREFERRED EMBODIMENT

Figure 1:
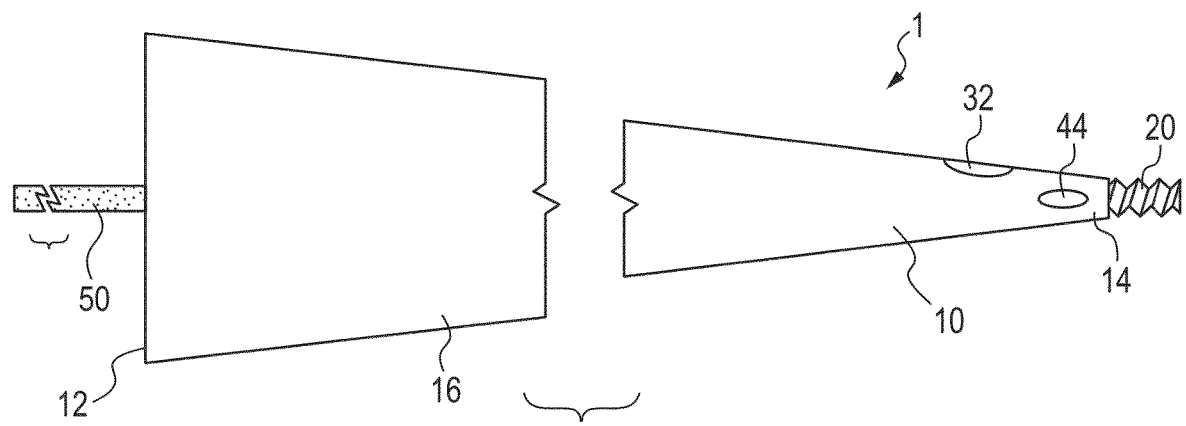
FIG. 1 is a fragmentary, side view of a preferred embodiment of the present invention.

Recognizing the need for an improved, urological dilator that can provide better guidance for the insertion of an indwelling catheter through a patient's urethra and into one's bladder, the present invention seeks to provide such an improved, urological device.

Various aspects, advantages and alternative and preferred embodiments may be included in the following description of the present invention. All patents, patent applications, published articles and documents and other things referenced herein are hereby incorporated by this reference in their entirety and for all purposes. To the extent of any inconsistency or conflict in the definition or use of terms between any of the incorporated publications, documents or things and the present application, those of the present application shall prevail.

Before explaining at least one embodiment of the present invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

FIG. 1 shows a fragmentary, side view of a preferred embodiment of the present invention 1. It is seen to be an improved, urological device that provides for the guided placement of the IDC-distal end of an indwelling catheter into a patient's bladder.

Figure 2:
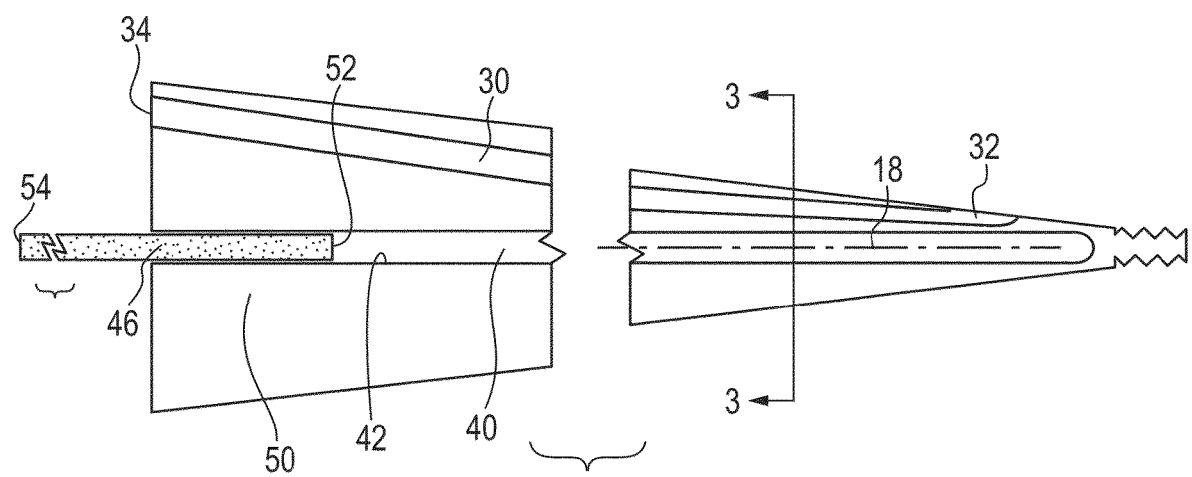
FIG. 2 is a fragmentary, longitudinal, cross-sectional view of a preferred embodiment shown in FIG. 1.

This improved, urological device includes a variable diameter, cylinder 10 that has a proximal 12 and a distal 14 end. The distance between these ends defines the cylinder's length. It also has an axial centerline 18 that extends between its ends, and a sloping (with respect to this centerline) outer surface 16 which reflects the fact that this cylinder's radius is not constant. At any point "x" along the length of this centerline, the radial distance between the centerline and the outer surface varies according to where this point "x" is located between the cylinder's ends, with this radius being larger at the cylinder's proximal end than at its distal end. See FIG. 2 which shows a fragmentary, longitudinal, cross-sectional view of a preferred embodiment shown in FIG. 1.

This variable diameter cylinder 10 is ideally fabricated from a semi-flexible, non-porous, fiberglass or other suitable (e.g., polytetrafluoroethylene, PTFE) material. Typical dimensions for this cylinder are in the ranges of: length=30-40 cm, diameters: 6-12 mm for the proximal end, and 3-6 mm for the distal end.

A connector 20 is attached to the cylinder's distal end. It is provided to allow for an easy connection to the complimentary connector that is found at the proximal end of the filiform or filiform-tipped guide wire that is normally used with a dilator. Typical threaded, connector lengths are in the range of 2.5-5.5 mm.

Figure 3:
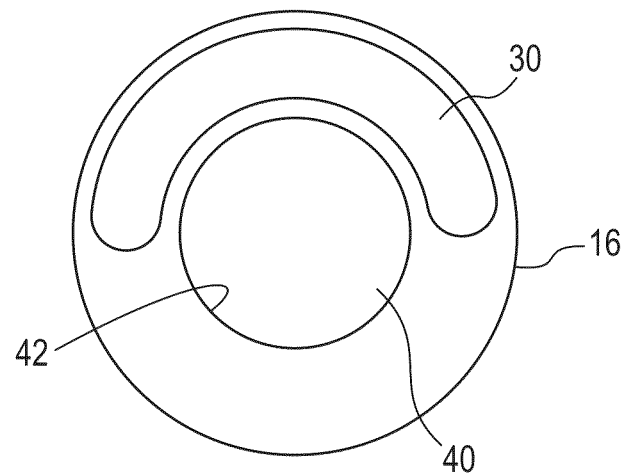
FIG. 3 is an axial, cross-sectional view of the preferred embodiment shown in FIG. 1 that is taken at the cross-section denoted by the numerals 3-3 in FIG. 2.

This cylinder is provided with a confirmation lumen 30 in order to confirm the placement of the device's distal end in a patient's bladder by the establishment of a flow of urine from a patient's bladder. This lumen has a confirmation opening 32, which is located proximate the cylinder's distal end, and a confirmation port 34, which is located proximate the cylinder's proximal end. See FIG. 3 which shows an axial, cross-sectional view of the preferred embodiment shown in FIG. 1 and with this view having been taken at the cross-section denoted by the numerals 3-3 in FIG. 2.

This cylinder also includes a guide wire lumen 40 that is located proximate the cylinder's axial centerline. It has an inner surface 42, a distal opening 44, which is located proximate the cylinder's distal end, and a proximal opening 46, which is located proximate the cylinder's proximal end.

Care should be taken in fabricating this inner surface to ensure that: (a) it is as smooth as possible and devoid of irregularities on which a guide wire could catch, thereby facilitating the easy movement of a guide wire through this lumen, and (b) its material of construction is chosen so as to make it hydrophilic (i.e., easily wetted by water; and therefore also urine) and to provide it with a low coefficient of friction (i.e., <0.15) with respect to the outer surface of the guide wire that will be passed through this lumen. These latter qualities can be achieved, for example, by providing this inner surface 42 with a polytetrafluoroethylene, PTFE, coating. Meanwhile, this lumen could also be constructed from PTFE and then inserted into an already formed cylinder.

Figure 4:
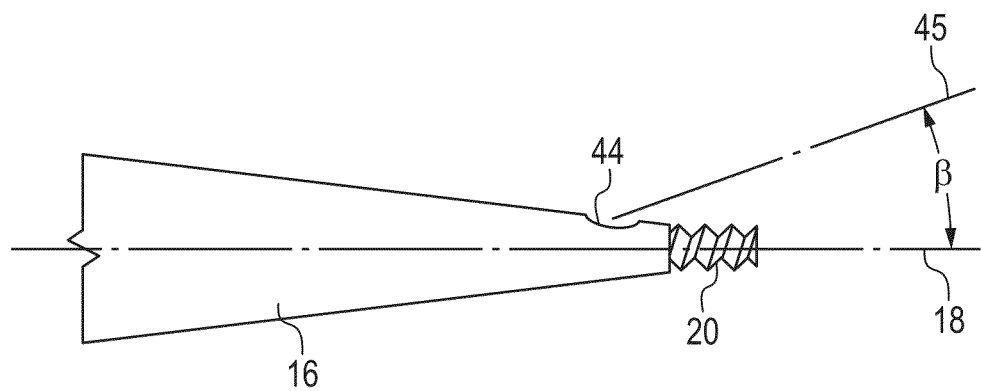
FIG. 4 is a fragmentary, side view of the distal end of the cylinder shown in FIG. 1 and after it has been rotated 90 degrees to show the difference in the directions of the axial centerlines of the cylinder and exiting the distal opening of the guide wire.

Special care also needs to be taken in constructing this lumen's distal opening 44 as it is desired that this opening be configured so as to allow the tip of the guide wire that exits it to be moving in a direction that is as close as possible to parallel to the direction of cylinder's axial centerline 18. Consequently, the guide wire lumen's distal opening is configured such that the angle Beta, β, between this exit's axial centerline (i.e., the distal opening's axial centerline at its exit or the "d-o-axial centerline") 45 and that of the cylinder's axial centerline 18 is generally less than approximately 30 degrees, and ideally less than 10 degrees. See FIG. 4. This arrangement has the benefit of reducing the resistance that the guide wire 50 experiences when it is passing through this opening 44.

Additionally, this lumen 40 was further configured to allow for or enable the careful withdrawal (without putting too much strain on the inserted guide wire 50 as to cause its distal end 52 to be withdrawn from a patient's bladder) of the cylinder 10 from a patient's urethra while leaving behind the gw-distal end 52 in the patient's bladder. Consequently, this now in-place, guide wire 50 can be used to guide the insertion of an indwelling catheter into a patient's bladder.

If a council tip, indwelling catheter (i.e., one with an end hole or port at the IDC-distal end of the catheter that connect this port to the catheter's lumen) is not readily available, the needed lumen can usually be provided by cutting the distal end of the indwelling catheter to create an access hole into the catheter's confirmation lumen. This hole then allows its edges to slide around the proximal end 54 of the in-place guide wire, thereby allowing the distal end of the indwelling catheter to slide up the guide wire 50 and into a patient's bladder.

The recommended guide wire 50 for use with the present invention has gw-distal 52 and gw-proximal 54 ends and the distance therebetween defines the guide wire's length. With guide wires available in the size range of 2-6 Fr, those chosen for use with the present invention typically have a size of approximately 2-3 Fr, e.g., 2.8 Fr or 0.91 mm (e.g., Amplatz Super Stiff, Boston Scientific). Their materials of construction include a stainless steel core, usually with a polytetrafluoroethylene, PTFE, coating.

Given these guide wires sizes, and the fact that the configuration of the guide wire lumen 40 was optimized based of these preferred sizes, it was found that, for reliable movement of the guide wire 50 through the lumen 40, the preferred ratio of the diameter of the guide wire lumen to that of the guide wire itself was in the range of 1.03-1.5, and more preferably in the range of 1.05-1.2. Additionally, it was found that a lumen 40 of the above proportioned size helped to prevent the possibility of the distal 52 end of the guide wire (i.e., gw-distal end) from folding back on the rest of the trailing guide wire as it was being passed through the guide wire lumen. Thus, when the present invention uses an approximate 0.91 mm diameter guide wire, it's lumen 40 is configured to have an approximate diameter of 1.0 mm.

The procedure that the present invention provides for inserting an indwelling catheter into a patient's bladder has many advantages. For example, the present invention eliminates the need for an invasive cystoscopy procedure (i.e., requiring an operating room and general anesthesia for the patient), thus enhancing patient safety. Meanwhile, the present invention's quick use decreases the chances of patient kidney damage from prolonged bladder distention, thereby expediting the healing process and significantly reducing healthcare costs. This innovation of the present invention is a milestone in urological care and its use will become standard practice once the present invention is available to urological service providers.

The foregoing is considered as illustrative only of the principles of the present invention. Further, since numerous modifications and changes will readily occur to those skilled in the art, it is not desired to limit the invention to the exact construction and operation shown and described herein. Accordingly, all suitable modifications and equivalents may be resorted to, falling within the scope of the invention that is set forth in the herein claims to the invention.

We claim:

1. A urological device that provides for the guided placement of the distal end of an indwelling catheter into a patient's bladder, said urological device comprising:
   a cylinder having a proximal and a distal end, an outer surface, and an axial centerline that extends between said ends,
   a connector attached to said cylinder distal end,
   a guide wire lumen having a guide wire lumen diameter in said cylinder and that has an inner surface, a distal opening which has a d-o-axial centerline protruding therefrom and with said distal opening being located proximate said cylinder distal end, and a proximal opening which is located proximate said cylinder proximal end,
   a guide wire having a guide wire diameter and a gw-distal end and a gw-proximal end, a confirmation lumen in said cylinder that has a confirmation opening, which is located proximate said cylinder distal end, and a confirmation port, which is located proximate said cylinder proximal end, and wherein said confirmation lumen is configured to drain urine from the bladder of said patient, and wherein said guide wire lumen is configured to first allow for the passage of said gw-distal end through said guide wire lumen and into said patient bladder and then the withdrawal of said cylinder from the urethra of said patient while leaving behind said gw-distal end in said urethra of said patient for use in the insertion of said indwelling catheter.

2. The urological device as recited in claim 1, wherein:
the ratio of said guide wire lumen diameter to that of said guide wire diameter is in the range of 1.03-1.5.

3. The urological device as recited in claim 1, wherein:
the ratio of said guide wire lumen diameter to that of said guide wire diameter is in the range of 1.05-1.1.

4. The urological device as recited in claim 1, wherein:
the angle, β, between said d-o-axial centerline said cylinder axial centerline is less than 30 degrees.

5. The urological device as recited in claim 2, wherein:
the angle, β, between said d-o-axial centerline said cylinder axial centerline is less than 30 degrees.

6. The urological device as recited in claim 3, wherein:
the angle, β, between said d-o-axial centerline said cylinder axial centerline is less than 30 degrees.

7. The urological device as recited in claim 1, wherein:
said guide wire lumen having a material of construction that is chosen so that said guide wire lumen inner surface is hydrophilic and has a coefficient of friction <0.15.

8. The urological device as recited in claim 2, wherein:
said guide wire lumen having a material of construction that is chosen so that said guide wire lumen inner surface is hydrophilic and has a coefficient of friction <0.15.

9. The urological device as recited in claim 3, wherein:
said guide wire lumen having a material of construction that is chosen so that said guide wire lumen inner surface is hydrophilic and has a coefficient of friction <0.15.

10. The urological device as recited in claim 4, wherein:
said guide wire lumen having a material of construction that is chosen so that said guide wire lumen inner surface is hydrophilic and has a coefficient of friction <0.15.

11. The urological device as recited in claim 5, wherein:
said guide wire lumen having a material of construction that is chosen so that said guide wire lumen inner surface is hydrophilic and has a coefficient of friction <0.15.

12. The urological device as recited in claim 6, wherein:
said guide wire lumen having a material of construction that is chosen so that said guide wire lumen inner surface is hydrophilic and has a coefficient of friction <0.15.

13. The urological device as recited in claim 1, wherein:
said connector is configured to attach to a connector of a filiform that is configured for aiding in a urethral catheterization.

14. The urological device as recited in claim 3, wherein:
said connector is configured to attach to a connector of a filiform that is configured for aiding in a urethral catheterization.

15. The urological device as recited in claim 12, wherein:
said connector is configured to attach to a connector of a filiform that is configured for aiding in a urethral catheterization.

16. A method that provides for the guided placement of the distal end of an indwelling catheter into a patient's bladder, said method comprising the steps of:
providing a cylinder having a proximal and a distal end, an outer surface, and an axial centerline that extends between said ends,
providing a connector attached to said cylinder distal end,
providing a guide wire lumen, having a guide wire lumen diameter, in said cylinder and that has an inner surface, a distal opening which has a d-o-axial centerline protruding therefrom and with said distal opening being located proximate said cylinder distal end, and a proximal opening which is located proximate said cylinder proximal end,
providing a guide wire having a guide wire diameter and a gw-distal end and a gw-proximal end,
providing a confirmation lumen in said cylinder that has a confirmation opening, which is located proximate said cylinder distal end, and a confirmation port, which is located proximate said cylinder proximal end, and wherein said confirmation lumen is configured to drain urine from the bladder of said patient, and
configuring said guide wire lumen to first allow for the passage of said gw-distal end through said guide wire lumen and into said patient bladder and then the withdrawal of said cylinder from the urethra of said patient while leaving behind said gw-distal end in said urethra of said patient for use in the insertion of said indwelling catheter.

17. The method as recited in claim 16, wherein:
the ratio of said guide wire lumen diameter to that of said guide wire diameter is in the range of 1.05-1.1.

18. The method as recited in claim 17, wherein:
the angle, β, between said d-o-axial centerline said cylinder axial centerline is less than 30 degrees.

19. The method as recited in claim 18, wherein:
said guide wire lumen having a material of construction that is chosen so that said guide wire lumen inner surface is hydrophilic and has a coefficient of friction <0.15.

20. The method as recited in claim 19, wherein:
said connector is configured to attach to a connector of a filiform that is configured for aiding in a urethral catheterization.

* * * * *